US012447002B2

(12) United States Patent
Xu et al.

(10) Patent No.: US 12,447,002 B2
(45) Date of Patent: Oct. 21, 2025

(54) DISTAL PROTECTION DEVICE AND MANUFACTURING METHOD THEREFOR

(71) Applicant: SUZHOU ZENITH VASCULAR SCITECH LIMITED, Suzhou (CN)

(72) Inventors: Xiangyu Xu, Suzhou (CN); Shuang Li, Suzhou (CN); Liyou Guo, Suzhou (CN); Jie Xia, Suzhou (CN)

(73) Assignee: SUZHOU ZENITH VASCULAR SCITECH LIMITED, Jiangsu (CN)

( * ) Notice: Subject to any disclaimer, the term of this patent is extended or adjusted under 35 U.S.C. 154(b) by 0 days.

(21) Appl. No.: 18/994,905

(22) PCT Filed: Jun. 7, 2024

(86) PCT No.: PCT/CN2024/101829

§ 371 (c)(1),
(2) Date: Jan. 15, 2025

(87) PCT Pub. No.: WO2024/230853

PCT Pub. Date: Nov. 14, 2024

(65) Prior Publication Data

US 2025/0262042 A1 Aug. 21, 2025

(30) Foreign Application Priority Data

May 6, 2023 (CN) ......................... 202310502337.1

(51) Int. Cl.
*A61F 2/01* (2006.01)

(52) U.S. Cl.
CPC ............ *A61F 2/0105* (2020.05); *A61F 2/011* (2020.05); *A61F 2230/0093* (2013.01); *A61F 2240/002* (2013.01); *A61F 2250/0067* (2013.01)

(58) Field of Classification Search
CPC ...... A61F 2002/018; A61F 2/01; A61F 2/013; A61F 2002/016; A61F 2/0105;
(Continued)

(56) References Cited

U.S. PATENT DOCUMENTS

| | | | |
|---|---|---|---|
| 2003/0109824 A1 | 6/2003 | Anderson et al. | |
| 2003/0130682 A1 | 7/2003 | Broome et al. | |

FOREIGN PATENT DOCUMENTS

| | | | |
|---|---|---|---|
| CA | 2448942 A1 | 5/2004 | |
| CN | 200980747 Y | 11/2007 | |

(Continued)

OTHER PUBLICATIONS

International Search Report and Written Opinion for corresponding PCT Application No. PCT/CN2024/101829, dated Sep. 14, 2024.

(Continued)

*Primary Examiner* — Katherine Shi
(74) *Attorney, Agent, or Firm* — K&L Gates LLP

(57) ABSTRACT

A distal protector includes a delivery guidewire assembly, an umbrella filter assembly and a coating assembly. The delivery guidewire assembly includes a delivery guidewire. The umbrella filter assembly includes an umbrella skeleton, a filter membrane and a fixed ring. The delivery guidewire detachably passes through the umbrella filter assembly. The fixed ring is disposed at a first end of the umbrella skeleton. The filter membrane covers the umbrella skeleton. A portion of the filter membrane being away from the first end of the umbrella skeleton is provided with filter holes. The coating assembly is disposed at a second end of the umbrella filter assembly being away from the fixed ring and includes a carrier and a thrombolytic drug carried in the carrier. The thrombolytic drug is configured to be released at a preset rate.

10 Claims, 4 Drawing Sheets

(58) Field of Classification Search
CPC ........ A61F 2230/008; A61F 2230/0006; A61F 2230/0067; A61F 2230/0093; A61F 2250/0067; A61F 2/90; A61B 17/12113; A61B 17/12172; A61B 2017/00526; A61B 17/12145; A61M 2025/1052; A61M 25/104; A61M 25/09
See application file for complete search history.

(56) References Cited

FOREIGN PATENT DOCUMENTS

| | | | |
|---|---|---|---|
| CN | 101843531 | A | 9/2010 |
| CN | 101861132 | A | 10/2010 |
| CN | 205339216 | U | 6/2016 |
| CN | 112773459 | A | 5/2021 |
| CN | 112790827 | A | 5/2021 |
| CN | 113081383 | A | 7/2021 |
| CN | 21490771 | U | 11/2021 |
| CN | 214907716 | U | 11/2021 |
| CN | 115670737 | A | 2/2023 |
| CN | 116439876 | A | 7/2023 |

OTHER PUBLICATIONS

First Chinese Office Action dated Nov. 12, 2003 for corresponding Chinese Application No. CN202310502337.1.
Second Chinese Office Action dated Jan. 29, 2024 for corresponding Chinese Application No. CN202310502337.1.
Notification to Grant Patent Right for Invention dated May 13, 2024 for corresponding Chinese Application No. CN202310502337.1, with English Translation.

DISTAL PROTECTION DEVICE AND MANUFACTURING METHOD THEREFOR

CROSS-REFERENCES TO RELATED APPLICATIONS

This is a National Stage Application, filed under 35 U.S.C. 371, of International Patent Application No. PCT/CN2024/101829, filed on Jun. 27, 2024, which is based on and claims priority to Chinese Patent Application No. 202310502337.1 filed with the China National Intellectual Property Administration (CNIPA) on May 6, 2023, the disclosures of which are incorporated herein by reference in their entireties.

TECHNICAL FIELD

The present application relates to the technical field of medical devices, for example, to a distal protector and a manufacturing method thereof.

BACKGROUND

"Stroke" is an acute cerebrovascular disease in which blood cannot flow to the brain due to sudden rapture or blockage of a blood vessel in the brain, causing brain tissue damage, and includes: ischemic stroke and hemorrhagic stroke. 60% of ischemic strokes are caused by a carotid artery stenosis that seriously threatens the quality of human life. Reasonable treatment of the carotid artery stenosis may effectively reduce the attack rate of the ischemic stroke.

During the process of a carotid artery stenosis operation, a thrombus may be detached, causing an intracranial cerebrovascular thrombus and leading to a stroke. Therefore, a temporary protector is placed at a distal end of the carotid artery stenosis during the treatment process of the carotid artery operation to collect the detached thrombus generated during the operation process to prevent the detached thrombus from flowing toward an intracranial blood vessel to form an embolism, effectively reducing the probability of a post-operative stroke.

Distal protectors are classified into two types. One is to weave a mesh through a weaving process, such as a nickel-titanium wire mesh, and the other one is to cover a filter membrane on an umbrella structure. The detached thrombus is collected through the nickel-titanium wire mesh or the filter membrane. However, when holes of the filter membrane and holes of the nickel-titanium wire mesh have relatively small diameters, blood cannot circulate. When the holes of the filter membrane and the holes of the nickel-titanium wire mesh have relatively large diameters, the filter membrane and the nickel-titanium wire mesh can only intercept and collect large thrombi, but microthrombi may pass through the filter membrane and the nickel-titanium wire mesh through gaps therein and cause secondary blockages at distant and finer blood vessels to form thrombi, leading to a serious consequence such as a stroke if the condition is serious.

SUMMARY

The present application provides a distal protector and a manufacturing method thereof so that the problem that thrombi are treated improperly through relatively large or small hole diameters can be solved.

The present application adopts the technical solutions below.

In an aspect, a distal protector is provided. The distal protector includes a delivery guidewire assembly, an umbrella filter assembly and a coating assembly.

The delivery guidewire assembly includes a delivery guidewire.

The umbrella filter assembly includes an umbrella skeleton, a filter membrane and a fixed ring, where the delivery guidewire detachably passes through the umbrella filter assembly, the fixed ring is disposed at a first end of the umbrella skeleton, the filter membrane covers the umbrella skeleton, and a portion of the filter membrane being away from the first end of the umbrella skeleton is provided with filter holes.

The coating assembly is disposed at a second end of the umbrella filter assembly being away from the fixed ring and includes a carrier and a thrombolytic drug carried in the carrier, where the thrombolytic drug is configured to dissolve a thrombus at a preset rate.

In some possible embodiments, the carrier includes a metal-oxide layer, where the metal-oxide layer is disposed on a surface of the second end of the umbrella filter assembly and provided with a plurality of receiving holes communicating with external environment, where the plurality of receiving holes are configured to receive the thrombolytic drug.

In some possible embodiments, the carrier further includes a hydrogel layer, where the hydrogel layer is disposed on a surface of one side of the metal-oxide layer facing away from the umbrella filter assembly and configured to seal the plurality of receiving holes.

In some possible embodiments, from a second end of the umbrella skeleton to the first end of the umbrella skeleton, the umbrella skeleton sequentially includes a collar, a first skeleton main body and a second skeleton main body that are sleeved on the delivery guidewire, the filter membrane covers the first skeleton main body, the second skeleton main body forms an opening, and the coating assembly is disposed on a surface of the collar.

In some possible embodiments, the first skeleton main body includes a first fitting portion and a connection portion.

The first fitting portion is adjacent to a first end of the umbrella filter assembly and is trumpet-shaped, the first fitting portion is configured to be attached to an inner wall of a blood vessel, a first end of the first fitting portion faces the second skeleton main body, a second end of the first fitting portion faces the connection portion, and a cross-sectional diameter of the first end of the first fitting portion is greater than a cross-sectional diameter of the second end of the first fitting portion.

The connection portion is adjacent to the second end of the umbrella filter assembly and connected to the collar.

Two ends of the second skeleton main body are connected to the first fitting portion and the fixed ring respectively.

In some possible embodiments, the first skeleton main body further includes a second fitting portion connected between the first fitting portion and the connection portion.

In some possible embodiments, the first skeleton main body is woven mesh-shaped, and the second skeleton main body includes a plurality of connection rods that are spaced apart, where each of the plurality of connection rods is disposed at an included angle with an axis of the fixed ring, and two ends of each of the plurality of connection rods are connected to the first fitting portion and the fixed ring respectively.

In some possible embodiments, two layers of filter membranes are provided and disposed on an inner side of the umbrella skeleton and an outer side of the umbrella skeleton respectively.

In some possible embodiments, the delivery guidewire assembly further includes a check ring sleeved on the delivery guidewire, and the first end of the umbrella filter assembly is limited at the delivery guidewire through the check ring.

In another aspect, a method for manufacturing a distal protector is provided. The method includes: forming an umbrella filter assembly, including: cutting, setting, and polishing an umbrella skeleton, where the umbrella skeleton includes a collar, a first skeleton main body and a second skeleton main body that are sequentially connected, connecting a first end of the umbrella skeleton to a fixed ring, covering a filter membrane on the first skeleton main body and configuring filter holes at a portion of the filter membrane being away from the fixed ring; making a delivery guidewire pass through the umbrella filter assembly; and coating a coating assembly on a surface of the collar of the umbrella filter assembly and a surface of the filter membrane of the umbrella filter assembly.

REFERENCE LIST

Figure 1:
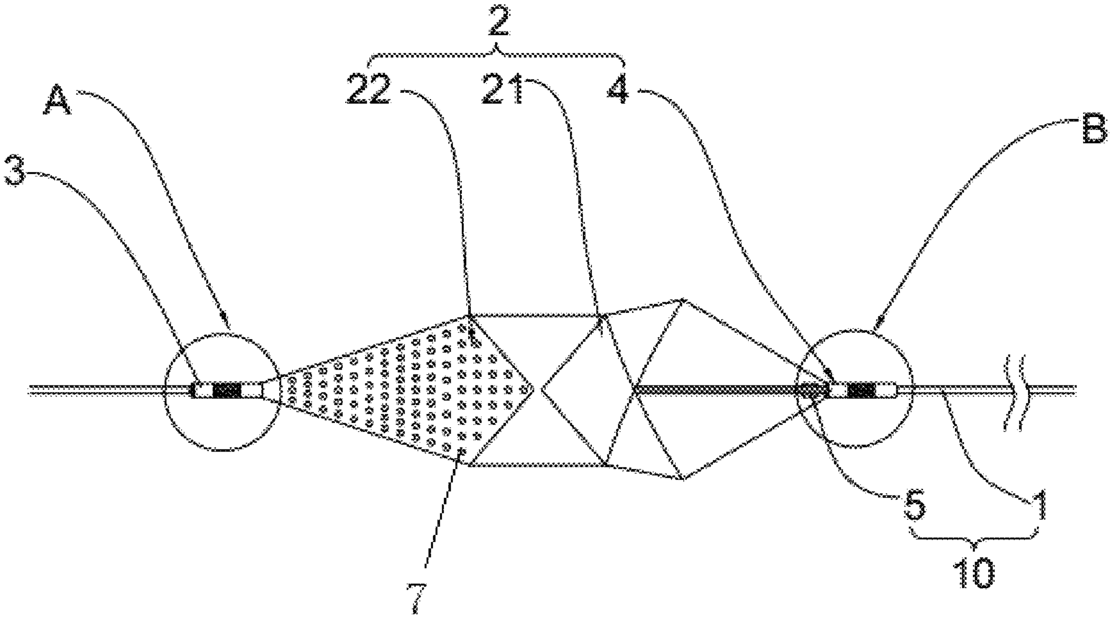
FIG. 1 is a view of a distal protector according to an embodiment of the present application.

10 delivery guidewire assembly
1 delivery guidewire
2 umbrella filter assembly
21 umbrella skeleton
211 collar
212 first skeleton main body
2121 first fitting portion
2122 second fitting portion
2123 connection portion
213 second skeleton main body
2131 connection rod
22 filter membrane
3 coating assembly
31 carrier
311 metal-oxide layer
3111 receiving hole
312 hydrogel layer
32 thrombolytic drug
4 fixed ring
41 middle sleeve
42 inner sleeve
5 check ring
6 development ring
7 filter hole
8 opening

DETAILED DESCRIPTION

Technical solutions in embodiments of the present application are described below in conjunction with the drawings. The embodiments described below are part, not all of the embodiments of the present application. Based on the embodiments of the present application, all other embodiments obtained by those skilled in the art without creative work are within the scope of the present application.

In the description of the present application, terms “joined”, “connected” and “fixed” are to be understood in a broad sense unless otherwise expressly specified and limited. For example, the term “connected” may refer to “fixedly connected”, “detachably connected”, or “integrated”, may refer to “mechanically connected” or “electrically connected”, or may refer to “connected directly”, “connected indirectly through an intermediary”, or “connected inside two elements” or “an interaction relation between two elements”. For those of ordinary skill in the art, specific meanings of the preceding terms in the present application may be understood based on specific situations.

In the present application, unless otherwise specified and limited, when a first feature is described as being “on” or “below” a second feature, the first feature and the second feature may be in direct contact or be in contact via another feature between the two features instead of being in direct contact. Moreover, when the first feature is described as being “on”, “above”, or “over” the second feature, the first feature is right on, above, or over the second feature, the first feature is obliquely on, above, or over the second feature, or the first feature is simply at a higher level than the second feature. When the first feature is described as being “under”, “below”, or “underneath” the second feature, the first feature is right under, below, or underneath the second feature, the first feature is obliquely under, below, or underneath the second feature, or the first feature is simply at a lower level than the second feature.

Figure 2:
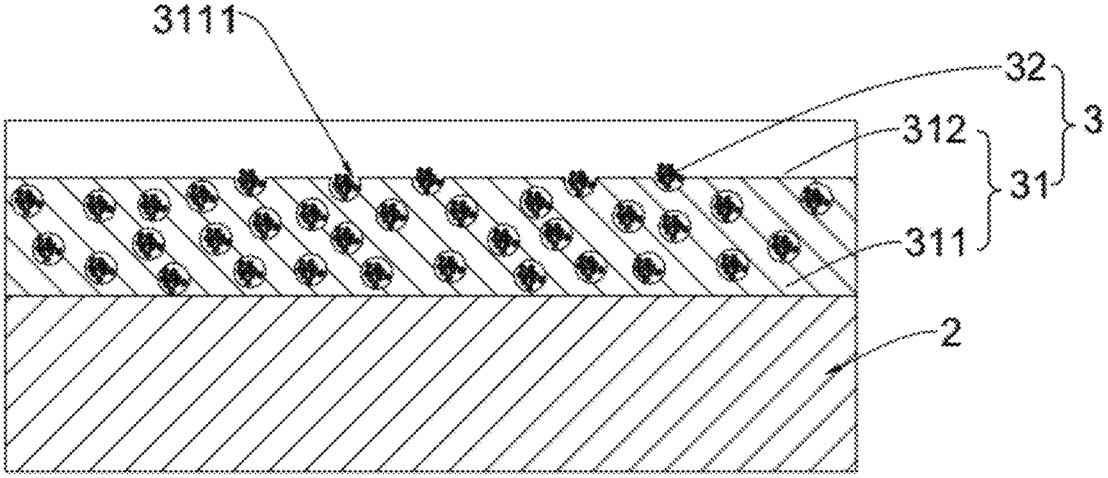
FIG. 2 is a partial cross-section view of a coating assembly connected to an umbrella filter assembly according to an embodiment of the present application.

This embodiment provides a distal protector. As shown in FIGS. 1 and 2, the distal protector includes a delivery guidewire assembly 10, an umbrella filter assembly 2 and a coating assembly 3. The delivery guidewire assembly 10 includes a delivery guidewire 1 and a check ring 5. The umbrella filter assembly 2 includes an umbrella skeleton 21, a filter membrane 22 and a fixed ring 4. The delivery guidewire 1 can detachably pass through the umbrella filter assembly 2. The fixed ring 4 is disposed at a first end of the umbrella skeleton 21 (that is, a proximal end of the umbrella skeleton 21). The proximal end of the umbrella skeleton 21 (one end of the umbrella skeleton 21 adjacent to the fixed ring 4) is trumpet-shaped. The filter membrane 22 covers the umbrella skeleton 21. A portion of the filter membrane 22 being away from the first end of the umbrella skeleton 21 is provided with filter holes 7. The coating assembly 3 is disposed at a distal end of the umbrella filter assembly 2 (that is, the coating assembly 3 is disposed at a second end of the umbrella filter assembly 2 being away from the fixed ring 4) and includes a carrier 31 and a thrombolytic drug 32 carried in the carrier 31. The thrombolytic drug 32 can be sustainably released from the carrier 31 and dissolve a thrombus at a preset rate.

The term “proximal end” or “distal end” refers to a relative position for an operator. Relatively speaking, a position close to the operator is the proximal end, and a position away from the operator is the distal end. During the operation, the distal protector is loaded on a deliverer, passes through the carotid artery stenosis with the deliverer and is released by the deliverer at the distal end of the carotid artery stenosis with a certain distance, the umbrella filter assembly 2 opens radially, and the detached thrombus is intercepted and collected by the filter membrane 22 when passing through an opening 8. After the operation, the umbrella filter assembly 2 contracts radially and is retracted into a recovery tube for removal, thereby achieving the purpose of collecting the detached thrombus. By disposing the thrombolytic drug 32 on the coating assembly 3, during the operation, the thrombolytic drug 32 is released from the carrier 31 to perform a thrombolysis treatment on an escaped microthrombus that is not intercepted and collected by the filter membrane 22. Compared with postoperative medication, this has a more direct targeted treatment effect, reduces the risk of a postoperative stroke, improves the effect of treating a thrombus in a blood vessel and lowers the requirement for diameters of the filter holes 7 of the filter membrane 22. The proximal end of the umbrella skeleton 21 is trumpet-shaped to fit the inner wall of the blood vessel to further prevent the thrombus from escaping.

The umbrella skeleton 21 is connected to the fixed ring 4. The fixed ring 4 is configured to fix a second skeleton main body 213. The delivery guidewire 1 passes through the fixed ring 4 and the umbrella skeleton 21. Optionally, the delivery guidewire assembly 10 is inserted into the umbrella filter assembly 2.

The sustained-release rate of the thrombolytic drug 32 may be set according to actual requirements and is not limited. The thrombolytic drug 32 may be alteplase (rt-PA) or urokinase and is not limited.

In an embodiment, as shown in FIG. 2, the carrier 31 includes a metal-oxide layer 311. The metal-oxide layer 311 is disposed on the surface of the distal end (the second end) of the umbrella filter assembly 2 and provided with multiple receiving holes 3111 communicating with the external environment. The multiple receiving holes 3111 are configured to receive the thrombolytic drug 32 and sustainably release the thrombolytic drug 32 to perform an immediate thrombolysis treatment on a tinier thrombus. Diameters at outlets of the multiple receiving holes 3111 may be reduced to reduce the rate of releasing the thrombolytic drug 32.

In an embodiment, as shown in FIG. 2, the carrier 31 further includes a hydrogel layer 312. The hydrogel layer 312 is disposed on one side of the metal-oxide layer 311 facing away from the umbrella filter assembly 2 and can seal the multiple receiving holes 3111. By disposing the hydrogel layer 312, when the distal protector is not used, the hydrogel layer 312 prevents the thrombolytic drug 32 within the multiple receiving holes 311 from being released; and during the operation, the hydrogel layer 312 dissolves in blood, and the multiple receiving holes 3111 are opened so that the thrombolytic drug 32 can be released.

Figure 3:
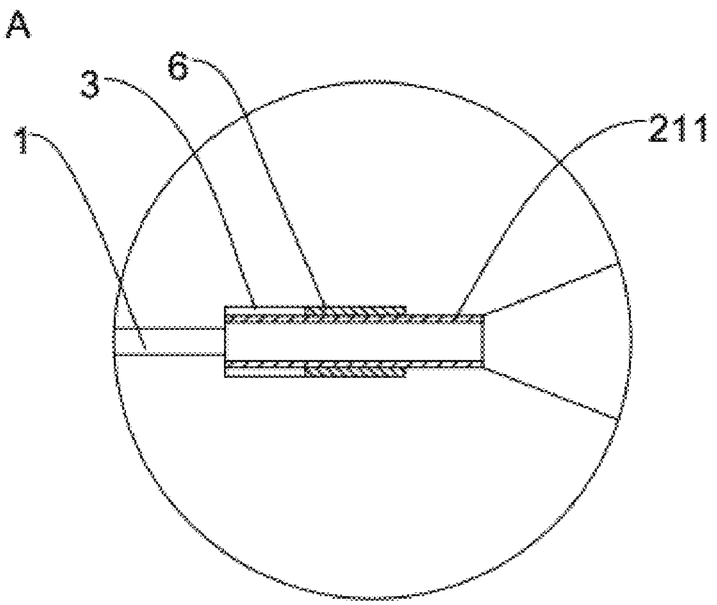
FIG. 3 is an enlarged view of part A in FIG. 1.
Figure 5:
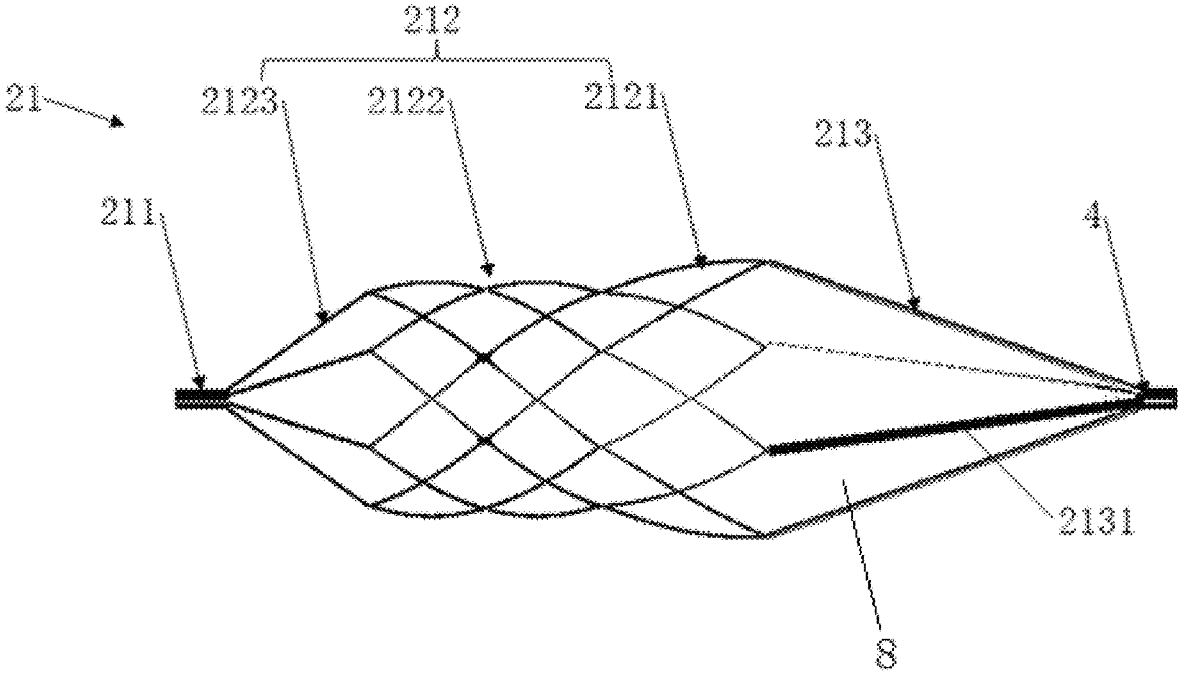
FIG. 5 is a view of the connection between an umbrella skeleton and a fixed ring according to an embodiment of the present application.

In an embodiment, as shown in FIGS. 3 and 5, the umbrella skeleton 21 includes a collar 211, a first skeleton main body 212 and the second skeleton main body 213 that are sequentially sleeved on the delivery guidewire 1, the filter membrane 22 covers the first skeleton main body 212, the second skeleton main body 213 forms the opening 8 through which the thrombus enters the umbrella filter assembly 2, and the coating assembly 3 is disposed on the collar 211. Specifically, the coating area of the coating assembly 3 on the collar 211 may be increased to increase the amount of the thrombolytic drug 32, or may be reduced to reduce the amount of the thrombolytic drug 32. Optionally, the thrombolytic drug 32 may also be disposed on the filter membrane 22 to increase the amount of the thrombolytic drug 32. This may be set according to requirements and is not limited.

Figure 4:
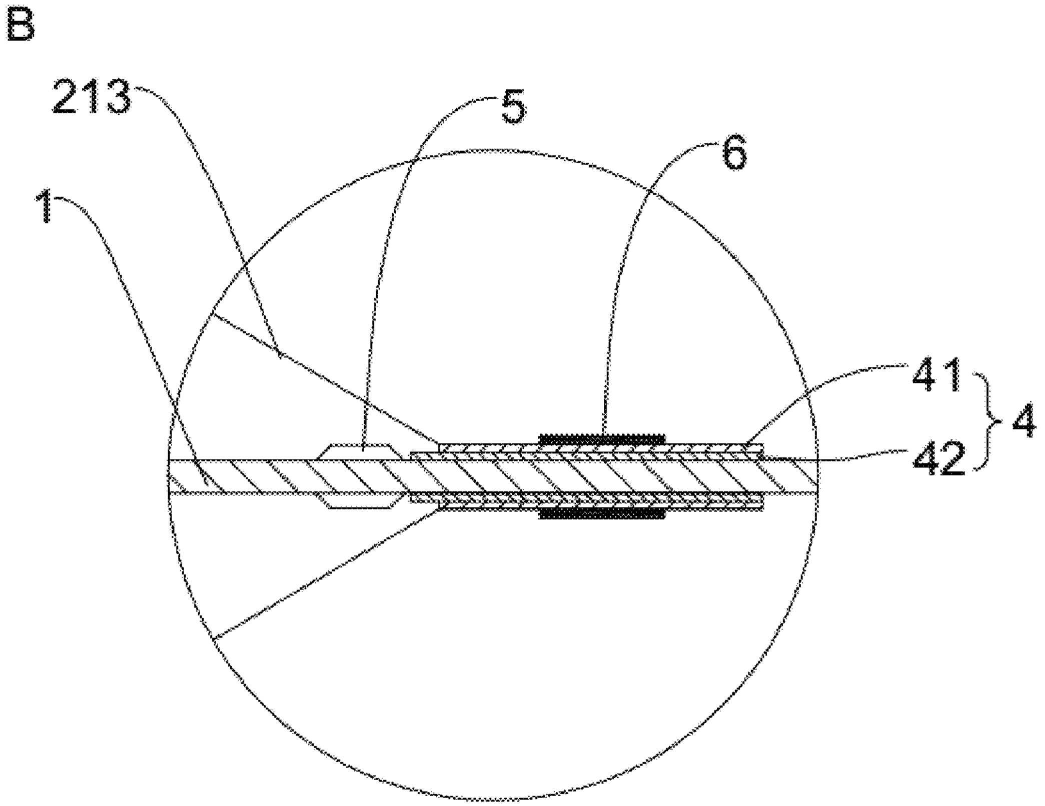
FIG. 4 is an enlarged view of part B in FIG. 1.

In an embodiment, as shown in FIGS. 3 to 5, the first skeleton main body 212 includes a first fitting portion 2121 and a connection portion 2123. The first fitting portion 2121 is adjacent to a first end of the umbrella filter assembly 2 and trumpet-shaped to enable the first fitting portion 2121 to fit the inner wall of the blood vessel to prevent the thrombus from escaping from between the inner wall of the blood vessel and the umbrella filter assembly 2. Moreover, a first end of the first fitting portion 2121 faces the second skeleton main body 213, a second end of the first fitting portion 2121 faces the connection portion 2123, and the cross-sectional diameter of the first end of the first fitting portion 2121 is greater than the cross-sectional diameter of the second end of the first fitting portion 2121; the connection portion 2123 is adjacent to the second end of the umbrella filter assembly 2 and connected to the collar 211; and two ends of the second skeleton main body 213 are connected to the first fitting portion 2121 and the fixed ring 4 respectively. By disposing the first fitting portion 2121 to be in the shape of a trumpet having an outwardly flared opening, when being connected to the second skeleton main body 213 and subjected to an inward radial force applied by the second skeleton main body 213, the first fitting portion 2121 is elastically deformed in the blood vessel, that is, an additional elastic force is added to enable a connection joint between the first fitting portion 2121 and the second skeleton main body 213 to better fit the inner wall of the blood vessel. In this manner, an included angle with certain degrees between the connection joint between the first fitting portion 2121 and the second skeleton main body 213 and the inner wall of the blood vessel can be prevented from being formed due to a pulling action applied by the second skeleton main body 213 when the first fitting portion 2121 is connected to the second skeleton main body 213, where the included angle will cause the formation of a triangle space, and the triangle space causes some thrombi to be received in the triangle space instead of being collected. This solution improves the rate of capturing thrombi by the umbrella filter assembly 2. The outer surface of the filter membrane 22 of the connection portion 2123 is provided with the thrombolytic drug 32.

As shown in FIG. 5, the first skeleton main body 212 further includes a second fitting portion 2122. One end of the second fitting portion 2122 is connected to the second end of the first fitting portion 2121, and the other end of the second fitting portion 2122 is connected to the connection portion 2123. By disposing the second fitting portion 2122, the fitting length between the umbrella filter assembly 2 and the inner wall of the blood vessel can be prolonged, and the fit can be increased.

In an embodiment, as shown in FIG. 5, the first skeleton main body 212 is woven mesh-shaped to increase the contact area between the first skeleton main body 212 and the filter membrane 22 and improve the connection reliability. The second skeleton main body 213 includes multiple connection rods 2131 that are spaced apart. Each connection rod 2131 is disposed at an included angle with the axis of the fixed ring 4. Two ends of the each connection rod 2131 are connected to the first fitting portion 2121 and the fixed ring 4 respectively. A gap between two adjacent connection rods 2131 forms the opening 8. The filter membrane 22 is disposed on the connection portion 2123 so that the thrombus can be intercepted. The filter membrane 22 is disposed on the first fitting portion 2121 and the second fitting portion

2122 so that the first skeleton main body 212 can be prevented from directly contacting the inner wall of the blood vessel, thereby reducing vasospasm. Without being provided with the filter membrane 22, the second skeleton main body 213 forms the blood flow opening.

In an embodiment, the umbrella skeleton 21 is shaped through cutting and then the shape of umbrella skeleton 21 is set, and the umbrella skeleton 21 is polished. The umbrella skeleton 21 can be axially stretched and radially compressed during the retraction process. The size of the umbrella skeleton 21 may be adjusted according to actual requirements, and the shape of the umbrella skeleton 21 remains unchanged. The polishing treatment ensures the smooth surface of the umbrella skeleton 21 and improves the fit.

In an embodiment, as shown in FIGS. 3 and 4, the distal protector further includes two development rings 6. The two development rings 6 are disposed on the collar 211 and the fixed ring 4 respectively and configured to display the current positions of two ends of the distal protector. As shown in FIG. 4, the fixed ring 4 includes a middle sleeve 41 and an inner sleeve 42. The middle sleeve 41 is configured to fix the second skeleton main body 213. The inner sleeve 42 is sleeved within the middle sleeve 41. The delivery guidewire 1 passes through the inner sleeve 42. The development ring 6 is sleeved on the middle sleeve 41. The development ring 6 and the middle sleeve 41 may jointly fix the second skeleton main body 213. This is not limited.

In an embodiment, as shown in FIGS. 1 and 4, the delivery guidewire 1 passes through the check ring 5, and when the delivery guidewire 1 passes through the umbrella filter assembly 2 from the second end to the first end, the first end of the umbrella filter assembly 2 can be limited at a distal end of the delivery guidewire 1 through the check ring 5 to prevent the umbrella filter assembly 2 from being disassembled from the distal end of the delivery guidewire 1. In an embodiment, the check ring 5 is located within the umbrella skeleton 21 and disposed between the collar 211 and the fixed ring 4 to achieve a limiting effect and prevent the umbrella filter assembly 2 from escaping from the delivery guidewire 1.

In an embodiment, two layers of filter membranes 22 are provided and disposed on an inner side of the umbrella skeleton 21 and an outer side of the umbrella skeleton 21 respectively. The two layers of filter membranes 22 can increase the toughness and better cover the umbrella skeleton 21 to prevent the umbrella skeleton 21 from directly contacting the blood vessel due to the separation of the two layers of filter membranes 22 from the umbrella skeleton 21, thereby reducing the vasospasm. The two layers of filter membranes 22 may be elastic members and can be stretched and deformed with the umbrella skeleton 21.

Figure 6:
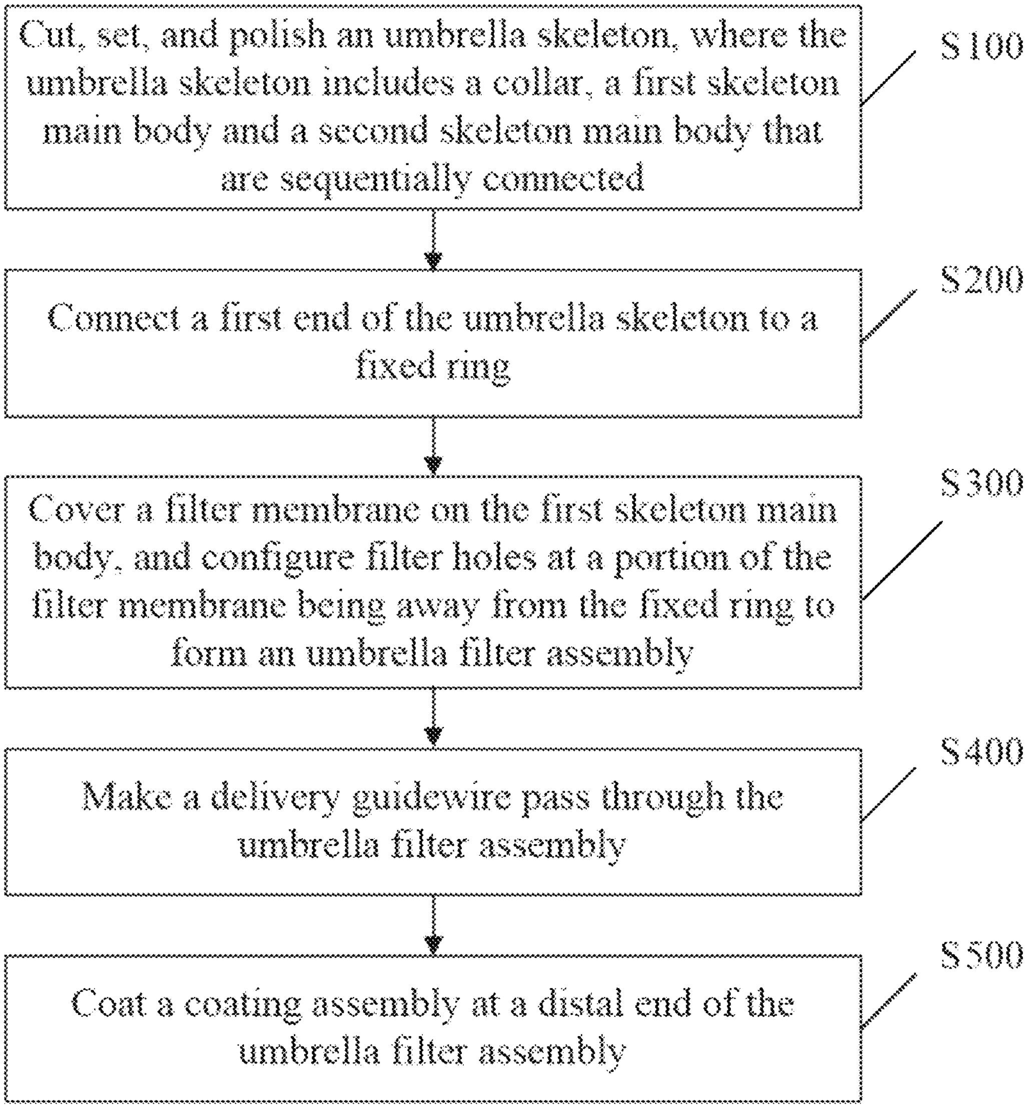
FIG. 6 is a flowchart of a method for manufacturing a distal protector according to an embodiment of the present application.

This embodiment further provides a method for manufacturing the preceding distal protector. As shown in FIG. 6, the method includes the following steps:

step S100, cutting, setting, and polishing an umbrella skeleton 21, where the umbrella skeleton 21 includes a collar 211, a first skeleton main body 212 and a second skeleton main body 213 that are sequentially connected;

step S200, connecting a first end of the umbrella skeleton 21 to a fixed ring 4;

step S300, covering a filter membrane 22 on the first skeleton main body 212, and configuring filter holes at a portion of the filter membrane 22 being away from the fixed ring 4 to form an umbrella filter assembly 2;

step S400, making a delivery guidewire 1 pass through the umbrella filter assembly 2; and step S500, coating a coating assembly 3 at a distal end of the umbrella filter assembly 2.

The umbrella skeleton 21 is formed into an integrated structure through shaping through cutting, setting and polishing, so the umbrella skeleton 21 has good structural reliability and is convenient to process. After the shape of the umbrella skeleton 21 is set, the umbrella skeleton 21 is covered by the filter membrane 22 and the coating assembly 3 to facilitate the adaptation of the filter membrane 22 and the coating assembly 3 to the appearance of the umbrella skeleton 21. In this manner, the structural precision is high, and the operation is convenient. The umbrella skeleton 21 includes the collar 211, the first skeleton main body 212 and the second skeleton main body 213. The first skeleton main body 212 includes a connection portion 2123, a second fitting portion 2122 and a first fitting portion 2121.

The filter membrane 22 further covers part of the collar 211.

The umbrella skeleton 21 is polished to ensure the smoothness of the surface of the umbrella skeleton 21 to facilitate the attachment of the umbrella skeleton 21 to the inner wall of the blood vessel.

The umbrella skeleton 21 is preliminarily set in S100, and the method further includes a step after S100 and before S200.

In S103, the first fitting portion 2121 is set as a trumpet.

That the coating assembly 3 is coated at the distal end of the umbrella filter assembly 2 includes the steps below.

In S501, the coating assembly 3 is coated outside the tube wall of the collar 211.

In S502, the coating assembly 3 is coated on the outer surface of the filter membrane 22.

After S100, the method further includes a step below.

In S600, one end of the second skeleton main body 213 facing away from the first skeleton main body 212 is bonded with an inner sleeve 42 and a middle sleeve 41. S600 may also be located after S300 or S500, which may be adjusted adaptively and is not limited.

After S100, the method further includes a step below.

In S700, a development ring 6 is bonded to the collar 211. S700 may also be located after S300 or S500, which may be adjusted adaptively and is not limited.

Optionally, S700 is located before S501, that is, after the development ring 6 is bonded to the collar 211, the coating assembly 3 is coated outside the tube wall of the collar 211.

After S600, the method further includes a step below.

In S800, a development ring 6 is bonded to the middle sleeve 41.

Optionally, S700 and S800 are performed successively to facilitate the bonding of the development rings 6 at the same station.

What is claimed is:

1. A distal protector, comprising:

a delivery guidewire assembly (10), comprising a delivery guidewire (1) and a check ring (5);

an umbrella filter assembly (2), wherein the umbrella filter assembly (2) comprises an umbrella skeleton (21), a filter membrane (22) and a fixed ring (4), the delivery guidewire assembly (10) is capable of detachably passing through the umbrella filter assembly (2), a proximal end of the umbrella skeleton (21) is trumpet-shaped, the filter membrane (22) covers the umbrella skeleton (21), and a distal portion of the filter membrane (22) fitting the umbrella skeleton (21) is provided with filter holes; and a coating assembly (3), wherein the coating assembly (3) is disposed at a distal end of the umbrella filter assembly (2) and comprises a carrier (31) and a thrombolytic drug (32) carried in the carrier (31), wherein the thrombolytic drug (32) is capable of being sustainably released from the carrier (31) at a certain rate, wherein the carrier (31) comprises a metal-oxide layer (311), the metal-oxide layer (311) is disposed on a surface of the distal end of the umbrella filter assembly (2) and provided with a plurality of receiving holes (3111) communicating with external environment, and the plurality of receiving holes (3111) are configured to receive the thrombolytic drug (32);

wherein the carrier (31) further comprises a hydrogel layer (312), and the hydrogel layer (312) is disposed on one side of the metal-oxide layer (311) facing away from the umbrella filter assembly (2) and capable of sealing the plurality of receiving holes (3111);

wherein the umbrella skeleton (21) comprises a collar (211), a first skeleton main body (212) and a second skeleton main body (213) that are sequentially sleeved on the delivery guidewire (1), the filter membrane (22) covers the first skeleton main body (212), the second skeleton main body (213) forms an opening, and the coating assembly (3) is disposed on the collar (211);

wherein the first skeleton main body (212) is woven mesh-shaped and comprises a first fitting portion (2121) and a connection portion (2123), the first fitting portion (2121) is trumpet-shaped and capable of fitting an internal wall of a blood vessel, a large end of the first fitting portion (2121) faces the second skeleton main body (213), a small end of the first fitting portion (2121) faces the connection portion (2123), the connection portion (2123) is connected to the collar (211), and two ends of the second skeleton main body (213) are connected to the first fitting portion (2121) and the fixed ring (4) respectively; and wherein the first skeleton main body (212) further comprises a second fitting portion (2122), and the second fitting portion (2122) is connected between the first fitting portion (2121) and the connection portion (2123).

2. The distal protector of claim 1, wherein the second skeleton main body (213) comprises a plurality of connection rods (2131) that are spaced apart, a connection rod (2131) of the plurality of connection rods is disposed at an included angle with an axis of the fixed ring (4), and two ends of the connection rod (2131) of the plurality of connection rods are connected to the first fitting portion (2121) and the fixed ring (4) respectively.

3. The distal protector of claim 2, wherein the check ring (5) is sleeved on the delivery guidewire (1), and the umbrella filter assembly (2) is capable of being limited at a distal end of the delivery guidewire (1) through the check ring (5).

4. A method for manufacturing the distal protector of claim 2, comprising:

cutting, setting, and polishing the umbrella skeleton (21), wherein the umbrella skeleton (21) comprises the collar (211), the first skeleton main body (212) and the second skeleton main body (213) that are sequentially connected;

covering the filter membrane (22) on the first skeleton main body (212) to form an umbrella filter assembly (2); and coating the coating assembly (3) at the distal end of the umbrella filter assembly (2).

5. The distal protector of claim 1, wherein the filter membrane (22) comprises two layers provided and disposed on an inner side of the first skeleton main body (212) and an outer side of the first skeleton main body (212) respectively.

6. The distal protector of claim 5, wherein the check ring (5) is sleeved on the delivery guidewire (1), and the umbrella filter assembly (2) is capable of being limited at a distal end of the delivery guidewire (1) through the check ring (5).

7. A method for manufacturing the distal protector of claim 5, comprising:

cutting, setting, and polishing the umbrella skeleton (21), wherein the umbrella skeleton (21) comprises the collar (211), the first skeleton main body (212) and the second skeleton main body (213) that are sequentially connected;

covering the filter membrane (22) on the first skeleton main body (212) to form an umbrella filter assembly (2); and coating the coating assembly (3) at the distal end of the umbrella filter assembly (2).

8. The distal protector of claim 1, wherein the check ring (5) is sleeved on the delivery guidewire (1), and the umbrella filter assembly (2) is capable of being limited at a distal end of the delivery guidewire (1) through the check ring (5).

9. A method for manufacturing the distal protector of claim 8, comprising:

cutting, setting, and polishing the umbrella skeleton (21), wherein the umbrella skeleton (21) comprises the collar (211), the first skeleton main body (212) and the second skeleton main body (213) that are sequentially connected;

covering the filter membrane (22) on the first skeleton main body (212) to form an umbrella filter assembly (2); and coating the coating assembly (3) at the distal end of the umbrella filter assembly (2).

10. A method for manufacturing the distal protector of claim 1, comprising:

cutting, setting, and polishing an umbrella skeleton (21), wherein the umbrella skeleton (21) comprises the collar (211), the first skeleton main body (212) and the second skeleton main body (213) that are sequentially connected;

covering the filter membrane (22) on the first skeleton main body (212) to form an umbrella filter assembly (2);

and coating the coating assembly (3) at the distal end of the umbrella filter assembly (2).

* * * * *